United States Patent
Patil

(10) Patent No.: US 11,420,937 B2
(45) Date of Patent: Aug. 23, 2022

(54) UREA PLANT WITH CHILLED CONDENSATION SECTION

(71) Applicant: STAMICARBON B.V., Sittard (NL)

(72) Inventor: Rahul Patil, Maastricht (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 17/424,940

(22) PCT Filed: Dec. 30, 2020

(86) PCT No.: PCT/NL2020/050824
§ 371 (c)(1),
(2) Date: Jul. 22, 2021

(87) PCT Pub. No.: WO2021/137699
PCT Pub. Date: Jul. 8, 2021

(65) Prior Publication Data
US 2022/0089528 A1   Mar. 24, 2022

(30) Foreign Application Priority Data
Dec. 30, 2019   (EP) .................................. 19220074

(51) Int. Cl.
*C07C 273/16* (2006.01)
*B01D 5/00* (2006.01)
(Continued)

(52) U.S. Cl.
CPC ............ *C07C 273/16* (2013.01); *B01D 5/006* (2013.01); *B01D 5/009* (2013.01); *B01D 5/0027* (2013.01);
(Continued)

(58) Field of Classification Search
USPC ................... 203/42, 73, 80; 159/24.3, 47.2; 202/185.2, 205; 564/73
See application file for complete search history.

(56) References Cited

U.S. PATENT DOCUMENTS 4,256,662 A * 3/1981 Gorlovsky ............ C07C 273/04
564/67
4,821,524 A 4/1989 Kostyal et al.
(Continued)

FOREIGN PATENT DOCUMENTS

CN   203578057 U   5/2014
EP      2192099 A1   6/2010
(Continued)

OTHER PUBLICATIONS

International Search Report and Written Opinion in corresponding International Patent Application No. PCT/NL2020/050824 dated Mar. 23, 2021. 9 pages.
(Continued)

*Primary Examiner* — Nina Bhat
(74) *Attorney, Agent, or Firm* — Leason Ellis LLP

(57) ABSTRACT

A urea production process comprising concentrating a first urea solution in a first vacuum evaporator in an evaporation section to give a urea melt and a first vapor, and condensing the first vapor in a first condensation section, wherein the first condensation section is a chilled condensation section, and a urea production system comprising the chilled condensation section.

14 Claims, 4 Drawing Sheets

(51) Int. Cl.
  *C07C 273/04*  (2006.01)
  *B01D 1/00*  (2006.01)
(52) U.S. Cl.
  CPC .......... *B01D 5/0054* (2013.01); *C07C 273/04* (2013.01); *B01D 1/0082* (2013.01)

(56) References Cited

U.S. PATENT DOCUMENTS

| | | | | |
|---|---|---|---|---|
| 5,744,009 | A * | 4/1998 | Singh | C07C 273/16 202/205 |
| 7,687,041 | B2 * | 3/2010 | Singh | B01J 19/32 261/114.5 |
| 9,458,098 | B2 * | 10/2016 | Mennen | B01J 10/00 |
| 10,370,326 | B2 | 8/2019 | Puci | |
| 10,486,125 | B2 | 11/2019 | Scotto | |
| 10,882,820 | B2 * | 1/2021 | Mostert | C07C 273/16 |
| 2009/0084149 | A1 | 4/2009 | Van Der Werf et al. | |
| 2011/0229394 | A1 * | 9/2011 | Niehues | C05C 9/005 422/187 |
| 2014/0206902 | A1 | 7/2014 | Mennen | |
| 2015/0133689 | A1 * | 5/2015 | Potthoff | C07C 273/16 422/187 |
| 2015/0133690 | A1 | 5/2015 | Mennen et al. | |
| 2016/0184758 | A1 | 6/2016 | Soons | |
| 2017/0312717 | A1 | 11/2017 | Scotto | |
| 2018/0326345 | A1 | 11/2018 | Doherty | |
| 2019/0185422 | A1 * | 6/2019 | Pustjens | B01D 5/0054 |
| 2021/0024460 | A1 | 1/2021 | Franzrahe | |

FOREIGN PATENT DOCUMENTS

| | | |
|---|---|---|
| EP | 3020702 A1 | 5/2016 |
| GB | 1528051 | 10/1978 |
| WO | 2010060535 A1 | 6/2010 |
| WO | 2013165245 A1 | 11/2013 |
| WO | 2013165246 A1 | 11/2013 |
| WO | 2014188371 A1 | 11/2014 |
| WO | 2021/137700 A1 | 7/2021 |
| WO | 2021/137701 A1 | 7/2021 |

OTHER PUBLICATIONS

International Preliminary Report on Patentability in corresponding International Patent Application No. PCT/NL2020/050824 dated Jun. 29, 2021. 11 pages.
International Search Report and Written Opinion in corresponding International Patent Application No. PCT/NL2020/050825 dated Mar. 23, 2021. 9 pages.
International Search Report and Written Opinion in corresponding International Patent Application No. PCT/NL2020/050826 dated Mar. 10, 2021. 11 pages.
International Preliminary Report on Patentability in corresponding International Patent Application No. PCT/NL2020/050826 dated Jun. 17, 2021. 12 pages.
Meessen. Ullmann's Encyclopedia of Industrial Chemistry. "Urea." Wiley-VCH Verlag GmbH & Co. KGaA, Weinheim (2010). 10.1002/14356007.a27_333.pub2. 39 pages.
No Author. "Urea Synthesis: A Status Report—I." Nitrogen No. 185, May-Jun. 1990. pp. 22-29.
Potthoff. "Innovative Ammonia Emission Reductions." Nitrogen +Syngas 294, Jul.-Aug. 2008, pp. 39-41. XP-002525996. 4 total pages.
Van Der Zande. "Zero waste urea production." Fertilizer Focus, Mar.-Apr. 2018. 3 pages.
Notice of Allowance for related U.S. Appl. No. 17/424,958, dated Mar. 10, 2022. 26 pages.

* cited by examiner

UREA PLANT WITH CHILLED CONDENSATION SECTION

CROSS-REFERENCE TO RELATED PATENT APPLICATIONS

This application is a U.S. National Stage Application under 35 U.S.C. § 371 of International Patent Application No. PCT/NL2020/050824 filed Dec. 30, 2020, which claims the benefit of priority of European Patent Application No. 19220074.9 filed Dec. 30, 2019, both of which are incorporated by reference in their entireties. The International Application was published on Jul. 8, 2021, as International Publication No. WO 2021/137699 A1.

FIELD

The invention pertains to the production of urea, in particular to the evaporation section of a urea plant.

INTRODUCTION

In an embodiment the invention pertains to a urea production process comprising concentrating a urea solution in a first vacuum evaporator comprised in an evaporation section to give a urea melt and vapor, and condensing said vapor in a condenser. The urea melt is for instance supplied to a finishing section such as a granulator or a prilling tower. In order to reach a low water content of the melt, such as less than 1.0 wt. % or less than 0.50 wt. % (these water contents are in particular useful in case of prilling), the first evaporator is operated at vacuum (a pressure less than 100 kPa), such as less than 20 kPa or less than 10 kPa. The first evaporator is for instance a downstream evaporator of a multiple-stage evaporation section with at least a second vacuum evaporator as upstream evaporator in the evaporation section. Herein, the term "upstream" and "downstream" refer to the flow of the urea solution. The upstream second evaporator is optional in the invention.

The vapor from the evaporator(s) is condensed and the condensate is purified because the condensate typically contains some urea, $NH_3$ and possibly $CO_2$. For instance, Ullmann's Encyclopedia of Industrial Chemistry, chapter Urea (2010) mentions that process condensate from the evaporation section of a urea plant contains typically 3-8 wt. % ammonia and 0.2-2 wt. % urea. The condensate is treated in a waste water treatment (WWT) (also known as process condensate treatment section), for instance with a hydrolyser and a desorber. In an example WWT section a hydrolyser is used for hydrolysis of urea using steam at 170° C. to 230° C. as well as a desorber based on steam stripping at 1 to 5 bar. Various types of WWT sections are described in Ullmann's Encyclopedia of Industrial Chemistry, chapter Urea (2010). The operation of a WWT section is very energy consuming. The cleaned condensate from the WWT often needs to be very pure as it can be used e.g. as boiler feed water for the urea plant, in order to raise steam used as heat transfer fluid in the urea plant.

FIG. 1 shows a reference urea production process not according to the invention. The evaporation section (EV) of the urea plant comprises at least a first evaporator (EV1) which has an inlet for a first urea solution (U1), an outlet for highly concentrated urea solution, in particular urea melt (UM) and a first vapor outlet (V1). The urea melt (UM) is for instance supplied to a prilling tower. The vapor outlet is connected to a first condensation section (C1) which uses cooling water (cw). The first vapor is transported to the first condensation section using a booster ejector (BEj) which uses steam (S1) that is mixed with the vapor sent to the condenser (C1), thereby increasing the pressure of the vapor. Hence, the steam is used as "live steam". The first condensation section (C1) has an outlet for condensate (PC1) connected to a wastewater treatment section (WWT), and an outlet for second vapor (V2) typically connected to an ejector (Ej1) for maintaining vacuum. In case of a multiple-stage evaporation section (EV) (as illustrated) the evaporations section further comprises the optional upstream second evaporator (EV2). The second evaporator has an outlet for urea solution (U1) connected to the inlet for urea solution of the first evaporator (EV1), an inlet for second urea solution (U2) and a vapor outlet (V3) (for third vapor) connected to a second condenser (C2). The second condenser (C2) uses cooling water. The second condenser has an outlet for (fourth) vapor (V4) connected to a second ejector (Ej2) for maintaining vacuum (both ejectors can be combined). The second condenser (C2) further has an outlet for condensate (PC2) connected to the wastewater treatment section (WWT). Except for the use of cooling water in the first condensation section and the booster ejector, these features apply equally for embodiments of the inventive process and plant.

US2015/0133690 discusses that the process condensate treatment of a urea plant requires valuable steam, i.e. is energy intensive, and that it is desired to minimize the amount of steam used in this section.

US2014/0206902 describes a urea production process with a prilling step, wherein two concentrators are used, wherein the downstream concentrator is operated at 1-10 kPa to give a urea melt with 99.2 to 99.9 wt. % urea and biuret. The downstream concentrator has an outlet for gas connected to a booster ejector which uses steam as a driving force. The boosted vapor from the booster ejector is supplied to a condenser. The document mentions that the concentrating section including the condensation and ejector equipment is bulky and heavy. The document teaches that by using three concentrators, a smaller booster ejector can be used.

CN203578057U describes a booster steam ejector that can be used in a urea plant.

The article "Urea synthesis: a status report—I" in Nitrogen No 185, May-June 1990 schematically shows a urea production process of the Stamicarbon $CO_2$-stripping process with a second stage evaporator connected to a vacuum condenser through a booster ejector. The document mentions that for the second evaporator operating at deep vacuum of 0.03 bar, some vacuum recompression back to 0.3 bar is needed to allow the moisture to be re-condensed before the vapors are mingled with those from the other evaporation stage.

There is a desire for urea production plants and processes which have improved energy efficiency.

SUMMARY

The invention pertains in a first aspect to a urea production process comprising concentrating a first urea solution in a first vacuum evaporator in an evaporation section to give a urea melt and first vapor, and condensing said first vapor in a first condensation section, wherein the first condensation section is preferably a chilled condensation section preferably using a cooling fluid other than water.

The invention also pertains to urea production plant comprising an evaporation section comprising a first evaporator and a first condensation section, wherein the first evaporator has an inlet for urea solution and an outlet for urea melt and an outlet for vapor connected to said first condensation section, wherein said first condensation section is preferably a chilled condensation section.

Figure 1:
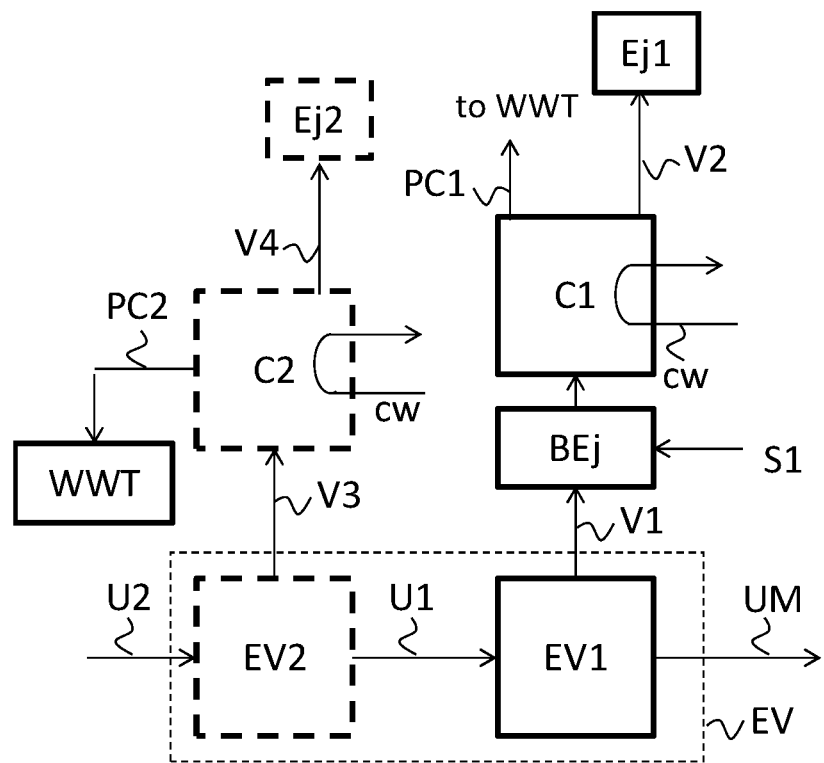
FIG. 1 schematically illustrates a reference process.

The embodiments illustrated in the figures are exemplary only and do not limit the invention.

DETAILED DESCRIPTION

The invention is broadly based on the judicious insight of using a chilled condensation section for an evaporator in an evaporation section of a urea plant. The chilled condensation section is preferably used for a downstream evaporator of a multiple-stage evaporation section, or for a sole evaporator of a single-stage evaporation section. Using such a chilled condensation section advantageously allows for omitting the booster ejector that is used for transporting the vapor from the evaporator to the condenser in known urea plants. Alternatively, if a booster ejector is still used, the amount of live steam introduced into the vapor for operating the booster ejector can be significantly reduced. By either omitting the booster ejector or using a smaller amount of live steam for operating the booster ejector, the volume of condensate is significantly reduced and the energy consumption in the WWT is accordingly reduced.

As used herein, for process streams (in particular urea solution), high pressure (HP) is at least 100 bara, e.g. 100 to 200 bara or 110-160 bara, medium pressure (MP) is 20-60 bara, low pressure (LP) is 4-10 bara. These pressure ranges are for process solutions and not necessarily the same for heating fluids such as steam. The abbreviation "bara" means bar absolute.

The inventive process comprising concentrating a first urea solution in a first vacuum evaporator in an evaporation section to give a urea melt and first vapor, and condensing said first vapor in a first condensation section, can be identified as a process for concentrating a urea solution, a process for preparing a urea melt, or more broadly as a urea production process. All preferences concerning the evaporation section and the condenser(s) apply equally to these types of processes. The preferences regarding the synthesis and recovery section concern the urea production process.

The term "process side" as used herein refers to the side of a heat exchanger receiving a process stream, such as the urea solution, vapor obtained from the urea solution, or condensate of such vapor.

The first evaporator preferably operates at a pressure of e.g. less than 20 kPa, less than 15 kPa or less than 10 kPa, and e.g. at a pressure of at least 1.0 kPa. In existing urea plants not according to the invention, usually booster ejectors are used for supplying vapor from an evaporator operating at such pressures to a condenser using cooling water. The first evaporator (which is connected to the chilled condenser) is for instance operated at a temperature of at least 130° C., such as at least 132° C., or at least 135° C. or at least 138° C., for instance up to 142° C. or up to 140° C., as liquid outlet temperatures. These temperatures are useful for obtaining highly concentrated urea melts having e.g. less than 5 wt. % or less than 1.0 wt. % moisture.

The first evaporator preferably operates at a pressure lower than the condensation pressure that can be achieved with the temperature of the cooling water available in the urea plant.

The condenser connected to the vapor outlet of the first evaporator is a chilled condenser and preferably uses a cooling medium (cooling fluid) other than water. The first condensation section can also be described as a first condenser. Typically, the condenser is a heat exchanger having a first side and a second side separated by at least a heat-exchanging wall. In the process of the invention, the vapor to be condensed is provided on the first side and chilled cooling medium is received on the second side. The first side and second side can, in addition to being separated by said wall, be separated by a further compartment for a heat transfer fluid such as water.

The term 'cooling medium' as used herein refers to a cooling fluid.

The chilled cooling medium is typically supplied to an inlet of the condenser, at said second side, from a chiller. In the chiller, the cooling medium is chilled, for instance by at least 5° C. or at least 10° C. and/or to a temperature of less than 25° C. The chilled cooling medium at the inlet of the first condensation section typically has a lower temperature than the cooling water that is used elsewhere in the urea plant and urea production process, e.g. at least 5° C. lower or at least 10° C. lower. Cooling water is for instance used in a second condenser connected to a second evaporator arranged upstream of the first evaporator. The chilled cooling medium at the inlet of the first condensation section typically has a temperature lower than the ambient temperature, e.g. at least 5° C. lower or at least 10° C. lower.

In some embodiments, the temperature of the cooling medium is for instance higher than 0° C. to avoid freezing of water in the process side of the condenser, and preferably the temperature of the cooling medium is at least 5° C., e.g. 5 to 10° C., e.g. at about 5° C., wherein the cooling medium is e.g. water or a compound other than water.

The chilled first condensation section or chilled first condenser can be described in terms of the cooling medium other than water, the temperature and/or the use of a chiller.

The chiller is for instance a vapor-compression refrigeration system, comprising a compressor, condenser, expansion valve, and evaporator, connected by a loop for cooling medium. In a preferred embodiment, chilling of the cooling medium in the chiller involves subjecting the cooling medium received in the vapor phase from the cooling fluid side of the first condensation section to compression to a higher pressure, condensation with heat withdrawal at said higher pressure, and expansion to a lower pressure to give chilled liquid cooling medium.

Further possible types of chillers are for instance based on absorption and regeneration.

In some embodiments, the chilled liquid cooling medium is brought in direct contact with a second side of the heat exchanging wall, which wall is on a first side in direct contact with vapor to be condensed.

In a further embodiment, a heat transfer fluid is used in the first condensation section for heat transport from the chilled cooling medium on the cooling fluid side to the vapor to be condensed on the process side. The first condensation section or first condensation section may comprise multiple heat exchangers in some embodiments. In this embodiment, the cooling medium is e.g. $NH_3$ and the chiller is e.g. comprised in an ammonia plant used for preparing $NH_3$ feed for the urea synthesis. This very elegantly allows for using an existing ammonia chiller of an ammonia plant as chiller for the first condensation section.

The chilled cooling medium is preferably a substance or composition other than water. Preferably, the cooling medium is a single substance (e.g. more than 99 wt. % purity) other than water. Preferably, the cooling medium comprises less than 1.0 wt. % water. Preferably, cooling medium comprises at least 95 wt. % of one or more compounds having a lower boiling point temperature (in the range of 1-10 bar) than water. The use of such compounds is advantageous for operating the chiller.

Preferably the cooling medium comprises $NH_3$ or a halogenated hydrocarbon.

The vapor transport line from the first evaporator to the first condensation section typically does not involve a booster ejector in the present invention.

The first evaporator operates preferably at substantially the same pressure (e.g. less than 10 kPa difference or less than 2.0 kPa difference), or at the same pressure, as the first condensation section to which it is connected (at the process sides).

Preferably, no water or steam is added to the first vapor between the first evaporator and the first condensation section. Preferably, the first vapor has a water content (wt. %) at the inlet of the first condensation section that is not higher, or is substantially the same (less than 10 percentage point difference or less than 1 percentage point difference) or is the same as the water content of the vapor at the outlet of the first vacuum evaporator.

In a preferred embodiment, the evaporation section is a multiple-stage evaporation section comprising an upstream second evaporator and the first evaporator connected to the chilled first condensation section. The second evaporator has an outlet for urea solution connected with an inlet for urea solution of the first evaporator. Such an evaporation section can for instance be used for preparing a urea melt with a moisture content of less than 1.0 wt. % or less than 0.50 wt. %, e.g. suitable for prilling and pastillation. In this embodiment, the first evaporator operates at the process side) at a lower pressure than the upstream second evaporator, preferably at least 5 kPa lower.

Preferably the evaporation section further comprises a second vacuum evaporator arranged upstream of the first vacuum evaporator such that urea solution is supplied from the second vacuum evaporator to said first vacuum evaporator.

The absolute pressure in the upstream second evaporator (at the process side) is for instance at least 1.5 times higher than the pressure in (the process side of) the first evaporator (e.g. the second evaporator operating at 15 kPa and the first evaporator operating at 10 kPa), or at least 2 times higher or at least 3 times higher. The upstream second evaporator operates for instance at a temperature of 120° C. to 130° C. at the process side. The downstream first evaporator (which is connected to the chilled condensation section or chilled condenser) is for instance operated at a temperature at least 5° C. higher than the upstream second evaporator, for instance at a temperature of at least 135° C. or at least 138° C., for instance up to 142° C. or up to 140° C.

The upstream second evaporator operates e.g. at an absolute pressure of at least 10 kPa and typically less than 90 kPa, e.g. 10 to 50 kPa or 15 to 30 kPa (at the process side). The upstream second evaporator operates e.g. at substantially the same pressure (e.g. less than 10 kPa difference or less than 2 kPa difference), or the same pressure, as the second condenser to which it is connected (at the process sides).

The downstream first evaporator operates at an absolute pressure of e.g. less than 20 kPa, less than 15 kPa or less than 10 kPa, and e.g. at a pressure of at least 1.0 kPa (at the process sides).

The evaporators typically are heat exchangers having a process side receiving the urea solution and a gas/liquid separator. The heat exchanger for instance has a heating fluid side (utility side) receiving heating fluid such as steam. However, in some embodiments the heat exchangers, e.g. the upstream second heat exchanger, receives process vapor on the utility side, which process vapor comprises $CO_2$ and $NH_3$ which are condensed thereby releasing heat. Such an evaporator may be provided by a condenser-evaporator.

The condensers typically are heat exchangers having a process side receiving vapor to be condensed and a cooling fluid side receiving a cooling fluid such as water or the chilled cooling medium. In an example embodiment, the condensers are shell-and-tube heat exchangers with cooling fluid in the tubes and vapor to be condensed in the shell.

In further embodiments, the evaporation section further comprises a third evaporator, for instance provided downstream (for urea solution) of the first evaporation, e.g. at the top of a prilling tower. In further embodiments, the evaporation section comprises the first evaporator (with the chilled condenser/chilled condensation section) and downstream thereof (for urea solution) an additional evaporator. In further embodiments, the evaporation section comprises e.g. an optional further evaporator between the second and the first evaporator. In some embodiments, the evaporation section comprises e.g. an optional further evaporator upstream of the second evaporator.

In a preferred embodiment of the multiple-stage evaporation section, the downstream first evaporator is operated at an absolute pressure of less than 10 kPa and the upstream second evaporator is operated at an absolute pressure of between 10 and 30 kPa, preferably to yield at the downstream first evaporator a urea melt with a water content of less than 1.0 wt. %, such as a urea melt suitable for prilling.

In an embodiment with a multiple stage evaporation section as described, the upstream second evaporator yields a concentrated urea solution that is supplied as first urea solution to the downstream first evaporator, as well as a second vapor. The second vapor is typically condensed in a second condenser which is e.g. a heat exchanger using a cooling water. The cooling water typically has a temperature of above 10° C. or above 15° C., for instance above 25° C. or above 30° C. In some embodiments, the cooling water as received by the second condenser has a temperature above the ambient temperature. Typically, the cooling water, in particular as received by the second condenser, has a temperature above $T_1$, wherein $T_1=T_a-5°$ C., wherein $T_a$ is ambient temperature.

The preferred upstream second vacuum evaporator has an outlet for vapor connected to a second condenser which preferably uses a second cooling fluid. Preferably the first condensation section is operated at a lower temperature at the condensate outlet than said second condenser, e.g. at least 5° C. lower or at least 10° C. lower. Preferably the condensate obtained from the first condensation section has a lower temperature than the condensate obtained from the second condenser, at the respective outlets of the condenser, e.g. at least 5° C. lower or at least 10° C. lower. Preferably the cooling medium of the first chilled condensation section has a lower temperature than the second cooling fluid of the second condenser, e.g. at least 5° C. lower or at least 10° C. lower, at the respective inlets of the condensers.

In a preferred embodiment, the downstream first evaporator is operated at an absolute pressure of less than 10 kPa and the upstream second evaporator is operated at an absolute pressure of between 10 and 30 kPa (both pressures at the process side). This provides an energy efficient configuration for preparing a urea melt with a water content of less than 1.0 wt. %, for instance starting from a urea solution having a water content of 10 to 40 wt. %.

This melt is preferably further processed in a prilling tower. Preferably, the process further comprises scrubbing the off-gas from the prilling tower in a scrubber and supplying the first condensate to the scrubber. Preferably the process further comprises supplying the second condensate from the upstream second condenser to the WWT. Preferably the scrubbing involves acid scrubbing with an inorganic or mineral acid giving utilized scrub liquid comprising an inorganic ammonium salt such ammonium sulphate or ammonium nitrate. Preferably this utilized scrub liquid is added to the first urea solution at a point downstream of the upstream second evaporator, e.g. in the supply line from the second to the first evaporator or in the first evaporator. In this way very elegantly contamination of the WWT with inorganic ammonium salts is avoided whereas the uses of a chilled condensation section instead of a booster ejector enables to supply the process condensate from the downstream first evaporator to the scrubber without overloading the scrubber with water.

The cooling water used in the second condenser is, as is usual for cooling waters in urea plants, cooled against ambient air. In other words, the (minimum) temperature of the available cooling water for the urea plant or process determines a minimum pressure of the second upstream condenser and second evaporator (on the process side). The maximum water content accepted by the finishing section sets a maximum pressure for the downstream first evaporator.

In a preferred embodiment, the process further comprises solidifying the melt in a finishing section to give solid urea and off-gas. The off-gas comprises e.g. air, urea dust and $NH_3$. The process preferably comprises scrubbing off-gas from the finishing section, e.g. prilling tower, in a scrubber using acid scrubbing to remove $NH_3$ from the off-gas, to give cleaned off-gas and utilized scrub liquid comprising ammonium salts. The process uses a multiple stage evaporation section as described with a first evaporator and an upstream second evaporator. The process furthermore comprises adding utilized scrub liquid comprising ammonium salts to the first to the first evaporator or to a supply line of the first evaporator at a point downstream of the second evaporator and upstream of or in the first evaporator. The process furthermore comprises supplying the first condensate from the first condensation section to the scrubber and supplying the second condensate from the second condenser to a wastewater treatment section. This elegantly provides for disposal of the utilized scrub liquid using relatively simple equipment in an energy efficient way. Preferably the downstream first evaporator is operated at an absolute pressure of less than 10 kPa. Preferably the upstream second evaporator is operated at an absolute pressure of between 10 and 30 kPa and/or preferably to give from the downstream first evaporator a urea melt with a water content of preferably less than 1.0 wt. %. The solid urea product comprises e.g. up to 5.0 wt. % ammonium salt, e.g. 0.10 to 3.0 wt. % and preferably contains at least 46 wt. % N.

In a preferred embodiment, the evaporation section is a multiple stage evaporation section as described with a first evaporator and an upstream second evaporator. The process furthermore preferably comprises adding an additive stream to the downstream first evaporator or to a supply line of the first evaporator at a point downstream of the second evaporator and upstream of or in the first evaporator. The additive stream comprises water and an additive compound. The additive compound is for instance a micronutrient or a compound comprising S or P, such as ammonium sulphate. The process furthermore comprises supplying the first condensate from the first condensation section to a unit other than the wastewater treatment section and supplying the second condensate from the second condenser to a wastewater treatment section. In a preferred embodiment, the process further comprises solidifying the melt in a finishing section to give solid urea and off-gas. The off-gas comprises e.g. air, urea dust and $NH_3$. The process preferably comprises scrubbing off-gas from the finishing section, e.g. prilling tower, in a scrubber using a scrub liquid, to give cleaned off-gas and utilized scrub liquid. Preferably the first condensate from the first condensation section is sent to the scrubber. This elegantly allows for preparing a solid urea product with a desirable additive, e.g. in an amount of at least 0.10 wt. % or at least 1.0 wt. % or at least 5 wt. % or at least 10 wt. % additive relative to total weight of the solid urea product. The solid urea product is e.g. a fertilizer. Preferably the downstream first evaporator is operated at an absolute pressure of less than 10 kPa. Preferably the upstream second evaporator is operated at an absolute pressure of between 10 and 30 kPa and/or to give a urea melt with a water content of preferably less than 1.0 wt. %.

The use of a chilled cooling medium is also advantageous in case the available cooling water is too hot or at risk of being too hot, e.g. for urea plants operating in hot environments such as in the Gulf Region. Accordingly, the invention also pertains to an embodiment wherein the evaporation section is a single-stage evaporation section and/or wherein the first evaporator receives urea solution with a water content of more than 10 wt. %, or more than 20 wt. %, typically less than 40 wt. %, and wherein the urea melt at the outlet of the first evaporator comprises e.g. more than 2 wt. % water or more than 5 wt. % water, typically less than 10 wt. % water and preferably maximum 5.0 wt. % water. In an embodiment the melt from the outlet of the first evaporator is used in a finishing section without further concentration or water removal. In such an embodiment, the finishing section is for instance a granulator. By using a urea plant with a chiller for the cooling medium of the first condensation section, the evaporation section can continue to operate even if a condenser using cooling water instead cannot provide a sufficiently low pressure for operation of the first evaporator.

The urea production process preferably comprises a step of providing an aqueous urea solution. In an embodiment, the process comprises reacting $NH_3$ and $CO_2$ under urea-forming conditions in a high pressure urea synthesis section so as to form a urea synthesis solution comprising urea, water, and ammonium carbamate, and removing ammonia and ammonium carbamate from said urea synthesis solution so as to give said urea solution. The removal preferably involves subjecting the urea synthesis solution to one or more dissociation steps in one or more decomposers for dissociating ammonium carbamate into $NH_3$ and $CO_2$ so as to give the aqueous urea solution. The dissociation steps are for instance carried out at high pressure (such as in case of a urea plant of the stripping type), medium pressure and/or low pressure. The dissociation steps involve heating and optionally the use of a strip-gas. Dissociation with stripping involves the counter-current contacting of the urea solution with a strip gas stream. The liberated $NH_3$ and $CO_2$ are condensed, typically in a condenser operated at the same pressure as the decomposer, into ammonium carbamate which is recycled to the urea synthesis. The dissociation at medium and low pressure is carried out in the so-called recovery section of the urea plant. The recovery section comprises for instance a low pressure decomposer, or a medium pressure decomposer with downstream thereof (for urea solution) a low pressure decomposer. Each decomposer has for instance a gas outlet connected to a carbamate condenser. The evaporation section is arranged downstream of the recovery section, with for instance a flash vessel and/or a storage tank between the recovery section and the evaporation section. The aqueous urea solution as received by the evaporation section typically comprises 60 to 90 wt. % urea, such as 65 to 85 wt. % urea. The aqueous urea solution comprises typically at least 5 wt. % water, preferably at least 10 wt. % water. The solution may comprise further substances such as ammonia.

The solution as received by the evaporation section is e.g. at atmospheric pressure.

The urea production process (e.g., the synthesis section and recovery section design) is not particularly restricted, for instance a process with a high pressure stripper can be used, wherein the high pressure stripper uses for instance $CO_2$ or $NH_3$ as strip gas, or self-stripping. A total recycle design or a partial recycle design without a high pressure stripper can also be used, or even a once-through design. Such designs are well known in the art and are described for instance in Ullmann's Encyclopedia of Industrial Chemistry, chapter Urea (2010). In a particular embodiment, the aqueous urea solution is provided by a urea process of the $CO_2$-stripping type with a high pressure stripper using $CO_2$ as strip gas, wherein for instance the stripped urea solution is directly supplied to an LP recovery section.

In a preferred embodiment, the first evaporator or, if used, the upstream second evaporator, receives an aqueous urea solution (comprising e.g. between 10 and 40 wt. % water), typically directly or indirectly from a recovery section of the urea plant. The urea solution is e.g. supplied from a low pressure recovery section, for instance, through a flash vessel (operating at sub-atmospheric or atmospheric pressure) and/or a storage tank).

The urea melt obtained from the concentrating step is e.g. supplied to a finishing step where it is solidified into a solid urea product. The inventive urea production process optionally further comprises the finishing step. The finishing step is for instance granulation in a granulator, prilling in a prilling tower, or pastillation. The granulator is for instance a fluidized bed or spouted bed granulator. The prilling involves creating urea melt droplets using a device arranged in the top of the prilling tower; the urea droplets solidify during their fall. The device is for instance a prilling bucket. Granulation and prilling both use cooling air and give a waste air stream in addition to the solid urea product. Pastillation also gives waste air. The waste air stream contains urea dust and $NH_3$. The waste air stream is for instance scrubbed, preferably using an acid scrub liquid to remove $NH_3$ and/or with dust scrubbing using a circulating urea-containing solution to remove urea dust. The scrubbing may give a utilized scrub liquid which may comprise urea and ammonium salts. This utilized scrub liquid is for instance sent to a dedicated evaporator as described in US 2015/0133690. The utilized scrub liquid comprising ammonium salts may also be disposed of in other ways.

A granulator typically requires the urea melt to have a water (moisture) content of e.g. at most 5 wt. %. The granulator operates for instance with a urea melt containing 1.0-5.0 wt. % or 1.0 to 3.0 wt. % water. Such a urea melt is optionally obtained in the present invention with a single-stage evaporation section with an evaporator operating at 20-50 kPa, or with a multiple-stage evaporation section, for instance with a two-stage evaporation section.

In a particular embodiment, the finishing involves prilling. Prilling usually requires the urea melt to have a water content of less than 1.0 wt. % or less than 0.50 wt. %.

In a further embodiment, the finishing comprises pastillation. Pastillation involves deposing urea melt droplets on a cooling belt, such that the droplets cool on the belt. The belt is for instance a cooled moving belt. An example method is described in US 2009/0084149. Pastillation is for instance carried out using a Rotoform® apparatus available from Sandvik Process Systems. Pastillation typically requires the urea melt to have less than 1.0 wt. % water, such as less than 0.30 wt. %. Such a urea melt is for instance obtained in the present invention with the described multiple-stage evaporation section.

The invention also pertains to a urea plant for carrying out the inventive process. The urea plant comprises the evaporation section as described and preferably also comprises the synthesis section and recovery section as described. The plant furthermore preferably comprises a finishing section as described. The evaporation section comprises the first evaporator having an inlet for first urea solution, an outlet for urea melt, and an outlet for first vapor that is connected to an inlet of the first condensation section, wherein the first condensation section is preferably a heat exchanger having the vapor to be condensed on a first side and cooling fluid on a second side, the condenser having an inlet for cooling fluid connected to an outlet of a chiller. The evaporators of the evaporation section comprise a heat exchanger (e.g. shell-and-tube heat exchanger) and a gas-liquid separator.

Figure 2:
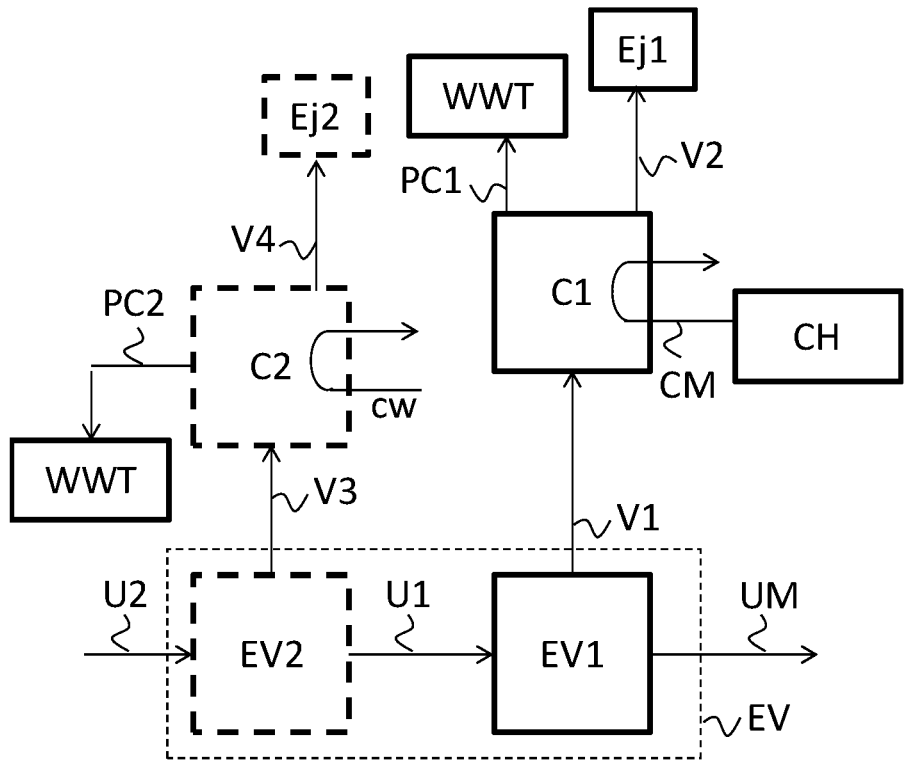
FIG. 2 schematically illustrates an example process and plant according to the invention.

FIG. 2 schematically illustrates an example urea production process and plant according to the invention. Compared to FIG. 1, the first condensation section (C1) uses a chilled cooling medium (CM) that is supplied by a chiller (CH). Moreover, as a strongly preferred feature, the booster ejector (BEj) is omitted and the first vapor (V1) is supplied directly from the first evaporator (EV1) to the first condensation section (C1). The first condensate (PC1) from the first condensation section (C1) is for instance supplied to the wastewater treatment section (WWT). In embodiments where the first condensate (PC1) from the first condensation section (C1) is supplied to the wastewater treatment section (WWT), omitting the booster ejector (BEj) in the transport line for the first vapor (V1) provides the advantage of reduced water load for the wastewater treatment section (WWT).

Figure 3:
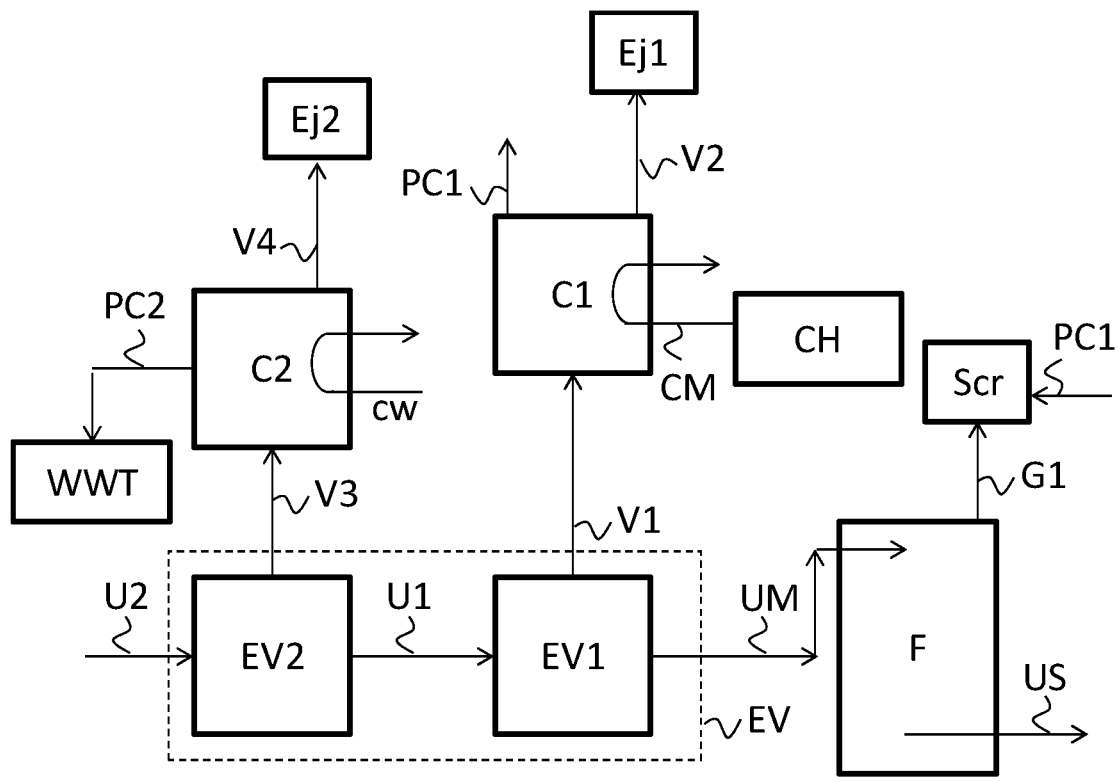
FIG. 3 schematically illustrates an example process and plant according to the invention.

FIG. 3 shows an alternative example embodiment. In this example, the evaporation section is a multiple-stage evaporation section further comprising the upstream second evaporator (EV2) connected to the second condenser (C2) The upstream second evaporator has an outlet for urea solution (U1) connected to the inlet for urea solution of the first evaporator (EV1) and an inlet for the upstream second urea solution (U2), the second urea solution (U2) is for instance supplied from a recovery section. The second condenser C2) has an outlet for second condensate (PC2) connected to the wastewater treatment section (WWT). In this embodiment, the liquid (in particular first condensate (PC1)) from the first condensation section (C1) is for instance supplied to a unit other than the wastewater treatment section (WWT), for instance a scrubber (Scr) that is used for scrubbing off-gas (G1) (waste air) from a finishing section (F) such as for example a prilling tower to which the urea melt is supplied. The urea melt is solidified in the prilling tower to form solid urea (US).

In the scrubber (Scr) the usually hot and dry off-gas (G1) is scrubbed with scrubbing liquid, including in this embodiment the first condensate (PC1) from the first condensation section (C1). The water evaporates for a large part in the scrubber (Scr) and is released in the atmosphere with the cleaned off-gas. The scrubber is for instance a dust scrubber, an acid scrubber, or a combined dust and acid scrubber. An acid scrubber uses an external supply of acid (such as sulphuric acid or nitric acid) for removal of $NH_3$ from the off-gas. A dust scrubber uses typically no external acid supply. The utilized scrub liquid from a dust scrubber typically does not contain ammonium salts such as ammonium nitrate and ammonium sulphate. An advantage of using a chilled cooling medium in this embodiment is that a booster ejector can be omitted and that relatively less liquid is withdrawn from the first condensation section, such that this liquid can be processed in a scrubber. The use of a booster ejector with live steam increases the amount of liquid obtained from the first condensation section such that this can be too much to be processed in a scrubber, making it necessary to send the liquid at least in part to a wastewater treatment section.

Figure 4:
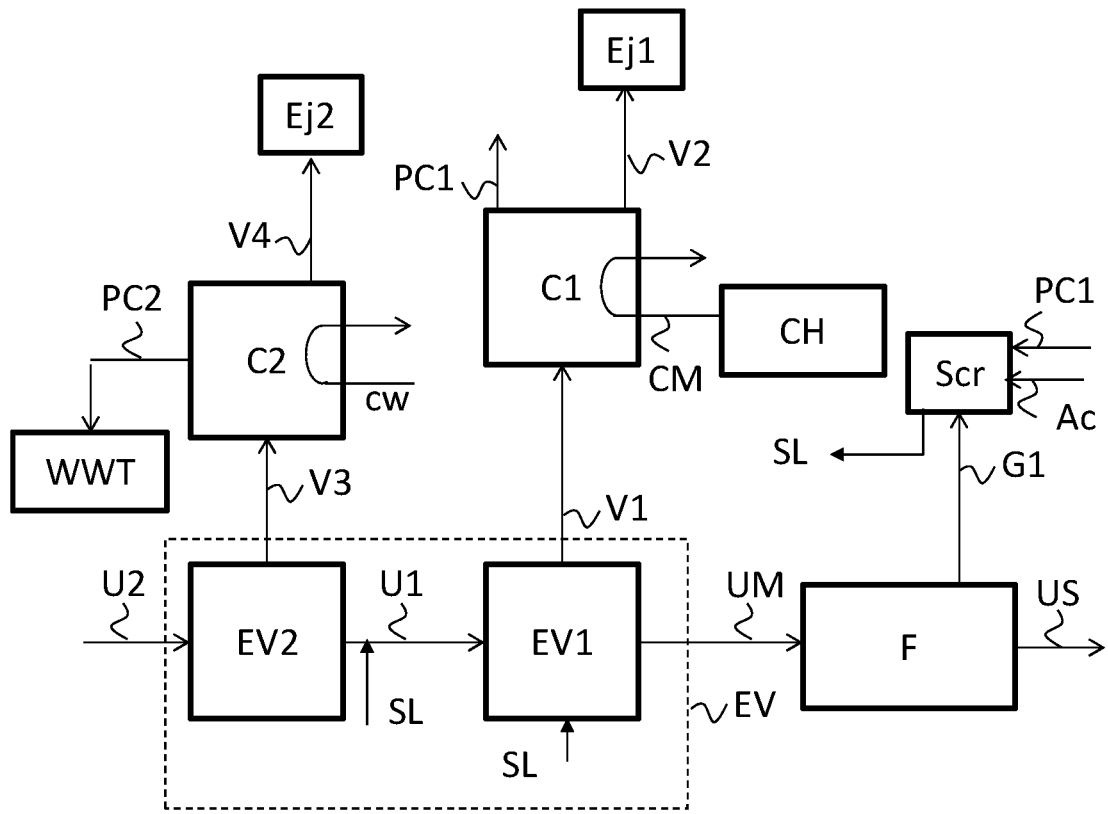
FIG. 4 schematically illustrates an example process and plant according to the invention.

FIG. 4 schematically shows an example process that is similar to the process of FIG. 3. The finishing section uses a urea melt with a water content of less than 5.0 wt. %, in particular less than 1.0 wt. %, and is for instance a prilling tower or pastillation device such as a Rotoformer™. The scrubber (Scr) is used for acid scrubbing with a supply of acid (Ac) to remove $NH_3$ from the off-gas (G1). The utilized scrub liquid (SL) is purged from the scrubber (Scr) and comprises an ammonium salt, e.g. ammonium sulphate or ammonium nitrate, and typically also dissolved urea (e.g. 10 to 60 wt. % urea). In a highly preferred embodiment, the utilized scrub liquid (SL) is supplied to a point in the plant downstream of the second evaporator and upstream of the first evaporator, such that it is received by the first evaporator but not by the second evaporator. The ammonium salts comprised in the utilized scrub liquid are incorporated in the urea melt and in the solid urea product, for instance in an amount of less than 1.0 wt. % ammonium salt relative to total solid urea product. A background reference for supplying utilized scrub liquid comprising ammonium salt to an evaporation section of a urea plant is Potthoff, Nitrogen+Syngas 294, p. 39. The utilized scrub liquid (SL) is for instance added to the first urea solution, for instance in the flow line from the second evaporator to the first evaporator, or for instance to an inlet of the downstream first evaporator.

The liquid from the first condensation section (which may contain the inorganic ammonium salts) is preferably sent to the scrubber and preferably not to the WWT, such that the WWT is not contaminated by these salts. The second condensate from the second condenser is preferably sent to the WWT. The amount of second condensate is e.g. too large to be added to the scrubber. The use of a chilled first condensation section advantageously provides for supplying the liquid from the first condensation section entirely to the scrubber without having excess liquid in the scrubber. If a booster ejector would be used for supplying the first vapor in the first condensation section, the amount of steam added by the booster ejector and ending up in the liquid from the first condensation section could be relatively large for handling in the scrubber or alternatively require the use of very excess cooling air in the finishing section. The water vapor is released in the cleaned off-gas from the scrubber.

Figure 5:
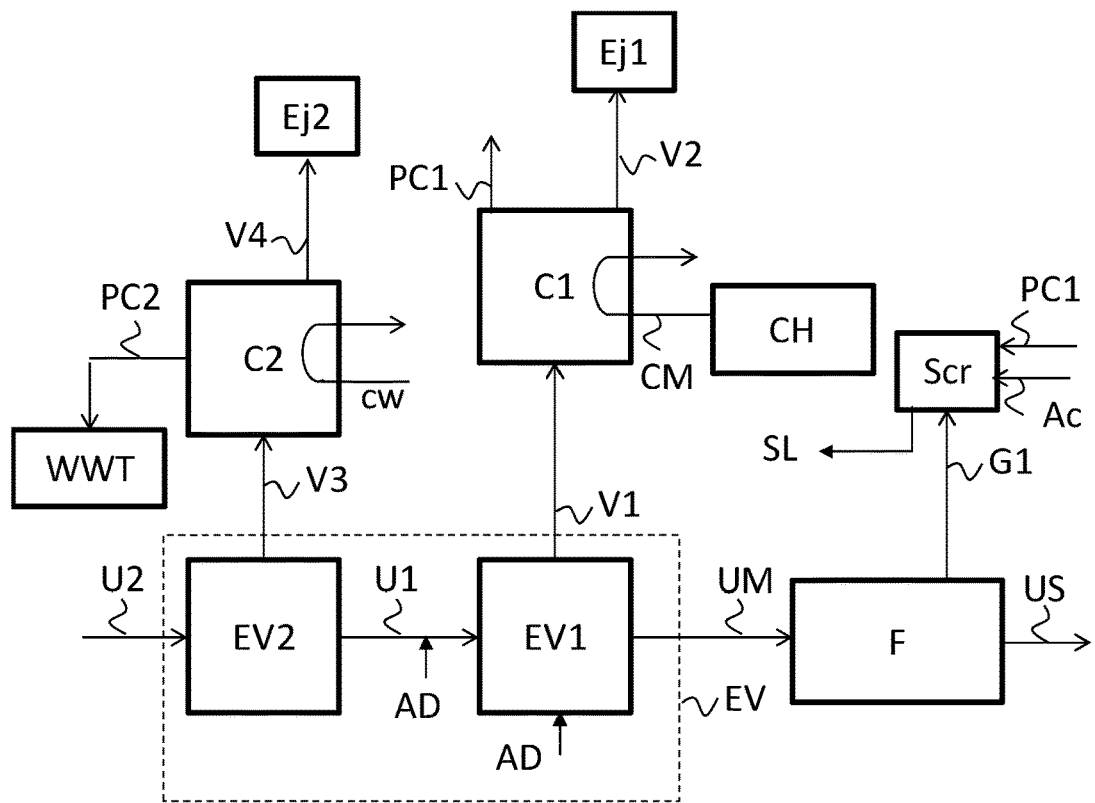
FIG. 5 schematically illustrates an example process and plant according to the invention.

FIG. 5 schematically illustrates an example process according to the invention wherein an additive solution (AD) is added to the first urea solution and/or to the first evaporator. The additive solution (AD) is for instance added to the supply line from the upstream second evaporator to the first evaporator. The additive solution or additive liquid stream comprises water and at least one additive compound other than urea. The additive compound is not volatile in the first evaporator and is incorporated in the urea melt and in the solid urea product after finishing. The additive compound is for instance a micro-nutrient or a compound, e.g. salt, containing S or P, such as ammonium sulphate or ammonium phosphate. The additive solution may comprise a plurality of additive compounds. Adding the additive compound as aqueous solution is for instance advantageous compared to adding solid additive compound to the urea melt or to the solid urea product, e.g. in order to ensure homogeneous incorporation. Adding the additive compound to a first downstream evaporator having a condenser with a liquid outlet connected to an inlet of the scrubber for treating off-gas from the finishing section, provides the advantage that the condensate which may contain traces of the additive does not contaminate the WWT. Adding the additive solution downstream of a second evaporator provides that most of the water from the urea solution obtained from a recovery section of the urea plant is already removed in the second upstream evaporator, such that the remaining smaller amount of water can be handled and removed in the scrubber.

The scrubber optionally uses acid scrubbing liquid (in case of acid scrubber) or optionally does not use acid scrub liquid (in case of only dust scrubbing). The multiple stage evaporation section is preferably of the type as discussed, preferably giving a urea melt with less than 1.0 wt. % water. In this embodiment, using a chilled first condensation section for the first evaporator is preferred over using a condenser operated with cooling water in order to maintain low pressure in the first evaporator preferably without using a booster ejector so as to no supply too much liquid from the first condensation section to the scrubber.

Figure 6:
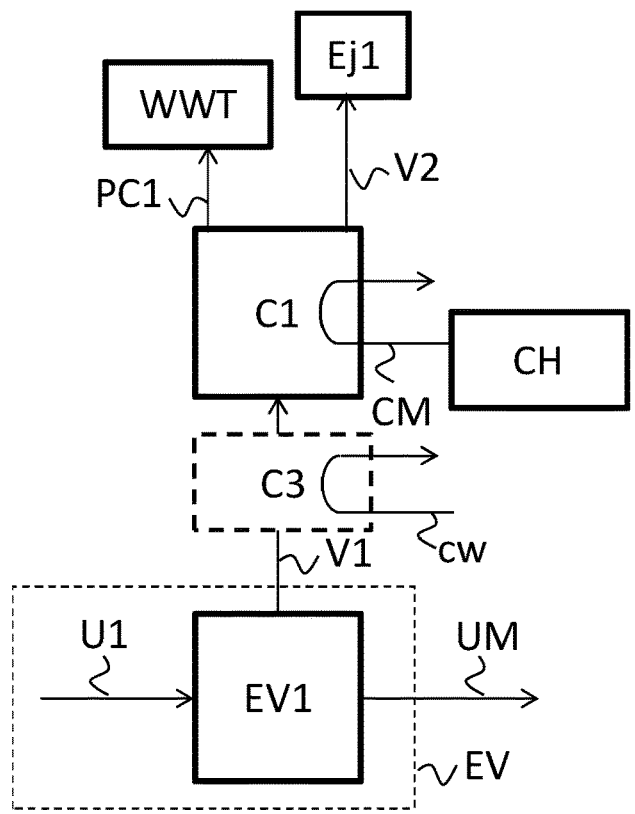
FIG. 6 schematically illustrates an example process and plant according to the invention.

FIG. 6 schematically illustrates an example process according to the invention wherein the evaporation section is a single-stage evaporation section. The urea melt is e.g. used for granulation and comprises e.g. 1-5 wt. % water, such as 3 to 5 wt. % water. The first evaporator (EV) is connected to first condensation section (C1) through an additional condenser (C3) such that the first vapor (V1) is in part condensed in the first condensation section (C1) and in part in the additional condenser (C3). The additional condenser (C3) uses e.g. cooling water (cw). The first condensation section (C1) and additional condenser (C3) are arranged in series for vapor and operate at substantially the same pressure on the process side. The first condensation section (C1) is arranged downstream (with respect to vapor flow) of the additional condenser (C3).

Figure 7:
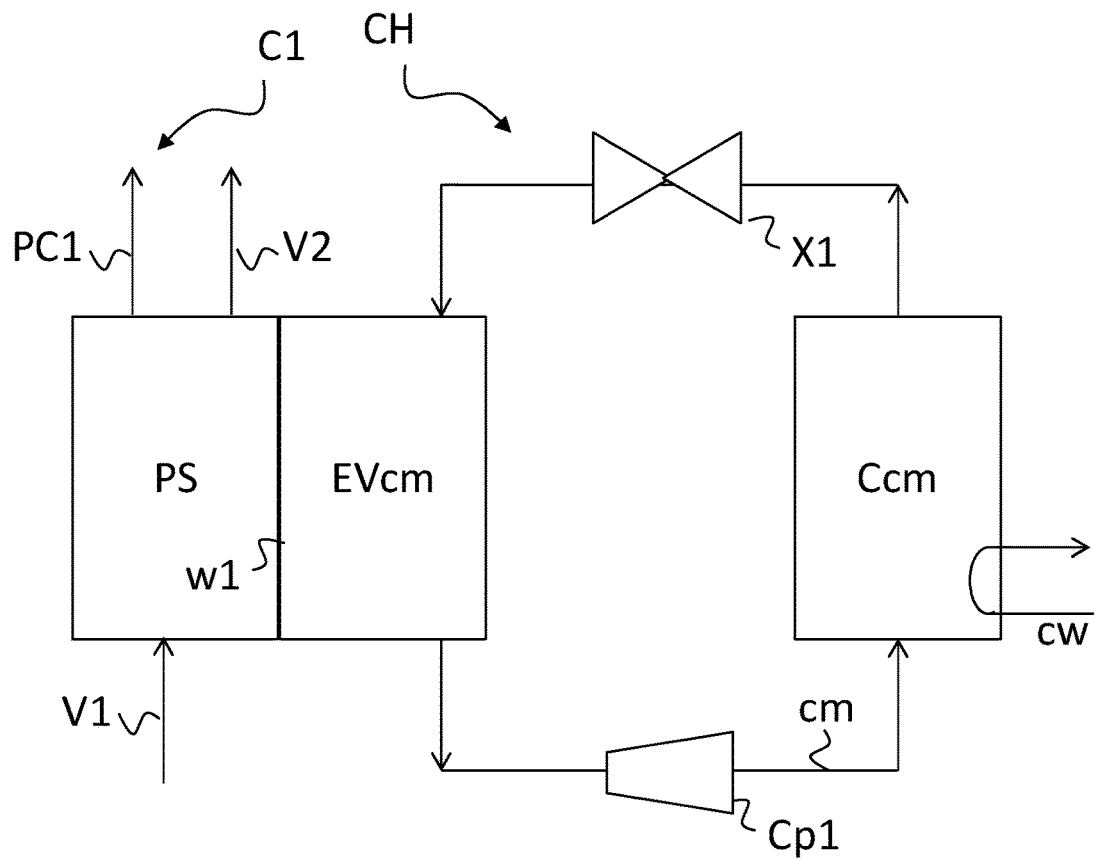
FIG. 7 schematically illustrates an example condenser and chiller useful in the process and plant of the present invention.

FIG. 7 schematically illustrates an example embodiment of the first condensation section and the chiller. The first condensation section (C1) is a heat exchanger where on the cooling fluid side the cooling medium (CM) evaporates, such that the cooling fluid side (e.g. shell space of a shell-and-tube heat exchanger with vapor to be condensed in the tubes) acts as evaporator (EVcm). The chiller comprises a condenser (Ccm) for condensing cooling medium, a compressor (Cp1) and an expansion valve (X1). The evaporated cooling medium is compressed in a compressor (Cp1) and condensed in a condenser (Ccm) which uses e.g. cooling water (cw). The condensed cooling medium is expanded to lower pressure in an expansion valve (X1) and returned to the cooling fluid side of the first condensation section. The process side (PS) of the first condensation section and the cooling fluid side are in heat exchanging contact, e.g. through a wall (w1).

Figure 8:
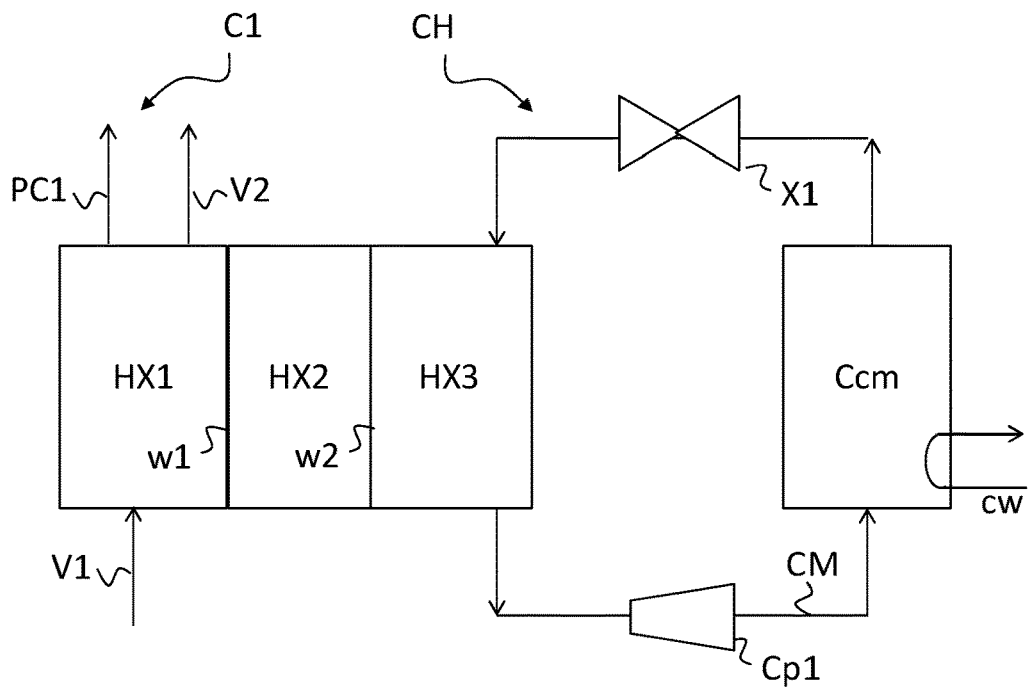
FIG. 8 schematically illustrates an example condenser and chiller useful in the process and plant of the present invention.

FIG. 8 schematically illustrates an example embodiment of the first condensation section or first condensation section and the chiller. The first condensation section (C1) comprises one or more heat exchangers and comprises a first compartment (HX1), a second compartment (HX2) and a third compartment (HX3). The chiller comprises a condenser (Ccm) for condensing cooling medium, a compressor (Cp1) and an expansion valve (X1).

The first and second compartment are in heat exchanging contact through a first wall (w1). The second and third compartment are in heat exchanging contact through a second wall (w2). The second compartment may provide for a spatial separation of the first and third compartment, e.g. the first and third compartment are provided in different units, such as in a first and a second heat exchanger respectively. The second compartment may comprise pipes or tubes, e.g. connecting said first and second heat exchanger. The first compartment has an outlet for the first vapor (V1) and an outlet for the first condensate (PC1). The third compartment has an inlet for cooling medium (CM) connected to the expansion valve (X1) and an outlet for cooling medium connected to the compressor (Cp1). The compressor has an outlet for cooling medium connected to a condenser (Ccm) which uses e.g. cooling water (cw). The second compartment in operation comprises a heat transfer fluid such as cooling water. In this way, the first condensation section (C1) uses the cooling medium (CM), which preferably a compound other than water, even though the first wall is not in contact with the cooling medium. In some embodiments, the first condensation section (C1) comprises a first and a second shell-and-tube heat exchanger, the first shell-and-tube heat exchanger receiving the first vapor (in the first compartment) and cooling water (in the second compartment), the second shell-and-tube heat exchanger receiving cooling medium (in the third compartment) and cooling water (in the second compartment). The first condensation section (C1) optionally comprises a first heat exchanger and a second heat exchanger, which are spatially separated from each other, wherein the first heat exchanger comprises the first compartment and a first part of the second compartment, and wherein the second heat exchange comprises a second part of the second compartment and the third compartment.

In conclusion, the invention pertains to a urea production process comprising concentrating a first urea solution in a first vacuum evaporator in an evaporation section to give a urea melt and first vapor, and condensing said first vapor in a first condensation section, wherein the first condensation section is a chilled condensation section.

The invention claimed is:

1. A urea production process comprising concentrating a first urea solution in a first vacuum evaporator in an evaporation section to give a urea melt and first vapor, and condensing said first vapor in a first condensation section, wherein the first condensation section is a chilled condensation section using a cooling fluid comprising at least 95 wt % of one or more compounds having a lower boiling point temperature than water in the range of 1-10 bar, wherein the first condensation section is a heat exchanger having a first side and a second side separated by at least a heat-exchanging wall, wherein chilled cooling fluid is supplied from a chiller to an inlet at said second side of the first condensation section and wherein the cooling fluid is chilled in the chiller to a temperature of less than 25° C.

2. A urea production process according to claim 1, wherein said evaporation section further comprises a second vacuum evaporator arranged upstream of said first vacuum evaporator such that urea solution is supplied from said second vacuum evaporator to said first vacuum evaporator.

3. A urea production process according to claim 1, wherein said first condensation section operates at the same pressure as said first vacuum evaporator.

4. A urea production process according to claim 1, wherein the first vapor has a water content at the inlet of the first condensation section that is the same as the water content of the vapor at an outlet of the first vacuum evaporator.

5. A urea production process according to claim 1, further comprising providing the urea solution, by:
A) reacting $NH_3$ and $CO_2$ under urea-forming conditions so as to give a urea synthesis solution comprising urea, water, ammonia, and ammonium carbamate,
B) removing ammonia and ammonium carbamate from said urea synthesis solution so as to give said urea solution.

6. A urea production process according to claim 1, wherein the cooling fluid comprises $NH_3$ or a halogenated hydrocarbon.

7. A urea production process according to claim 2, wherein the upstream second vacuum evaporator has an outlet for vapor connected to a second condenser, wherein the first condensation section has a first outlet for condensate, wherein the second condenser has a second outlet for condensate and wherein the first outlet for condensate has a lower temperature than the second outlet for condensate.

8. A urea production process according to claim 2, wherein said first vacuum evaporator is operated at an absolute pressure of less than 10 kPa and wherein said upstream second evaporator is operated at an absolute pressure of between 10 and 30 kPa, to give a urea melt with a water content of less than 1.0 wt. %, wherein the process further involves solidifying the urea melt in a finishing section to form solid urea.

9. A urea production process according to claim 8, wherein the finishing section is a prilling tower.

10. A urea production process according to claim 8, wherein the process further comprises scrubbing off-gas from the finishing section in a scrubber using acid scrubbing, and adding utilized scrub liquid comprising ammonium salts to the first vacuum evaporator or to a supply line of the first vacuum evaporator at a point downstream of the second vacuum evaporator and upstream of, or in, the first vacuum evaporator, and supplying a first condensate from the first condensation section to the scrubber and supplying a second condensate from the second condenser to a wastewater treatment section.

11. A urea production process according to claim 1, wherein the first condensation section comprises a first compartment, a second compartment and a third compartment, wherein the first compartment and the second compartment are in heat exchanging contact through a first wall and the second compartment and the third compartment are in heat exchanging contact through a second wall, wherein the first compartment has an inlet for the first vapor and an outlet for a first condensate, the third compartment has an inlet for cooling fluid and an outlet for cooling fluid and wherein the second compartment comprises cooling water.

12. A urea production process according to claim 11, wherein the first condensation section comprises a first heat exchanger and a second heat exchanger, which are spatially separated from each other, wherein the first heat exchanger comprises the first compartment and a first part of the second compartment, and wherein the second heat exchanger comprises a second part of the second compartment and the third compartment.

13. A urea production process comprising concentrating a first urea solution in a first vacuum evaporator in an evaporation section to give a urea melt and first vapor, and condensing said first vapor in a first condensation section, wherein the first condensation section is a chilled condensation section using a cooling fluid comprising at least 95 wt % of one or more compounds having a lower boiling point temperature than water in the range of 1-10 bar, wherein the first condensation section is a heat exchanger having a first side and a second side separated by at least a heat-exchanging wall, wherein chilled cooling fluid is supplied from a chiller to an inlet at said second side of the first condensation section and wherein the cooling fluid is chilled in the chiller by at least 5° C.

14. A urea production system comprising an evaporation section comprising a first evaporator and a first condensation section, wherein the first evaporator has an inlet for urea solution and an outlet for urea melt and an outlet for vapor connected to said first condensation section, wherein said first condensation section is a chilled condensation section, further comprising a chiller, wherein the first condensation section is a heat exchanger having a first side configured for receiving said vapor to be condensed and a second side having a cooling fluid inlet connected to an outlet of said chiller, and a cooling fluid outlet connected to an inlet of said chiller, and wherein the chiller comprises a compressor connected to said cooling fluid outlet of said first condensation section, a condenser connected to an outlet of said compressor, and an expansion valve having an inlet connected to said condenser and an outlet connected to said cooling fluid inlet of said first condensation section.

* * * * *